(12) United States Patent
Selker et al.

(10) Patent No.: US 9,050,379 B2
(45) Date of Patent: Jun. 9, 2015

(54) BIOPROCESS DATA MANAGEMENT

(75) Inventors: Mark Selker, Los Altos Hills, CA (US);
Charles Kamas, San Jose, CA (US);
Barbara Paldus, Woodside, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 759 days.

(21) Appl. No.: 12/321,657

(22) Filed: Jan. 22, 2009

(65) Prior Publication Data

US 2009/0273447 A1 Nov. 5, 2009

Related U.S. Application Data

(63) Continuation-in-part of application No. 12/150,806, filed on May 1, 2008, now abandoned.

(60) Provisional application No. 60/928,179, filed on May 8, 2007.

(51) Int. Cl.
*G11C 17/00* (2006.01)
*A61L 2/08* (2006.01)
*A61L 2/00* (2006.01)
*A61L 2/24* (2006.01)

(52) U.S. Cl.
CPC ............... *A61L 2/081* (2013.01); *A61L 2/0035* (2013.01); *A61L 2/24* (2013.01); *A61L 2202/14* (2013.01)

(58) Field of Classification Search
CPC ..... A61L 2202/24; A61L 2/081; B65B 55/16; G06K 19/077; G06K 19/07749; G11C 11/16; G11C 11/22
See application file for complete search history.

(56) References Cited

U.S. PATENT DOCUMENTS

| | | | |
|---|---|---|---|
| 5,892,706 A | 4/1999 | Shimizu | |
| 6,340,588 B1 * | 1/2002 | Nova et al. | 506/16 |
| 6,515,919 B1 | 2/2003 | Lee | |
| 6,532,346 B2 * | 3/2003 | Gallivan | 399/12 |
| 7,007,541 B2 | 3/2006 | Henry et al. | |
| 7,044,911 B2 * | 5/2006 | Drinan et al. | 600/300 |
| 7,256,695 B2 * | 8/2007 | Hamel et al. | 340/572.1 |

(Continued)

FOREIGN PATENT DOCUMENTS

| WO | WO 03/026724 | 4/2003 |
|---|---|---|
| WO | WO 03/044521 A | 5/2003 |

OTHER PUBLICATIONS

Web definitions—calibration—accessed Feb. 28, 2012, Google, https://www.google.com/search?q=define%3A+calibration &sourceid=ie7&rls=com.microsoft:en-us:IE-SearchBox&ie= &oe=.*

(Continued)

*Primary Examiner* — Daniell L Negron
*Assistant Examiner* — John Bamert
(74) *Attorney, Agent, or Firm* — Weaver Austin Villeneuve & Sampson LLP

(57) ABSTRACT

A data management system for a biological process, comprising:
  a. a single-use component,
  b. a tag assembly, including a non-volatile memory storage component, that is associated with the single-use component,
  c. the memory storage component including a unique identification and a memory, and at least one data element that describes a key performance, calibration or control parameter of the single-use component
  d. a memory reader useable to obtain the identification from the memory storage component.

18 Claims, 10 Drawing Sheets

(56) References Cited

U.S. PATENT DOCUMENTS

| | | |
|---|---|---|
| 7,524,304 B2 | 4/2009 | Genosar |
| 8,405,508 B2 * | 3/2013 | Burke ........................ 340/572.1 |
| 2002/0161460 A1 | 10/2002 | Noguchi |
| 2002/0188259 A1 * | 12/2002 | Hickle et al. .................. 604/189 |
| 2003/0072676 A1 * | 4/2003 | Fletcher-Haynes et al. .... 422/23 |
| 2005/0171738 A1 | 8/2005 | Kadaba |
| 2005/0205658 A1 | 9/2005 | Baker et al. |
| 2005/0242950 A1 | 11/2005 | Lindsay et al. |
| 2006/0079862 A1 | 4/2006 | Genosar |
| 2006/0142651 A1 * | 6/2006 | Brister et al. ................. 600/347 |
| 2006/0226985 A1 | 10/2006 | Goodnow et al. |
| 2007/0176773 A1 | 8/2007 | Smolander |
| 2007/0200703 A1 | 8/2007 | Baker et al. |
| 2008/0024310 A1 * | 1/2008 | Baker et al. ................. 340/572.8 |
| 2008/0114228 A1 * | 5/2008 | McCluskey et al. .......... 600/365 |
| 2008/0282026 A1 | 11/2008 | Selker et al. |
| 2009/0204250 A1 * | 8/2009 | Potyrailo et al. .............. 700/109 |

OTHER PUBLICATIONS

International Search Report dated Nov. 17, 2008 in PCT Application No. PCT/US2008/005615.

Written Opinion dated Nov. 17, 2008 in PCT Application No. PCT/US2008/005615.

EP Office Action dated Mar. 7, 2013 in EP Application No. 08754173.6.

US Office Action dated Aug. 3, 2011 in U.S. Appl. No. 12/150,806.

* cited by examiner

BIOPROCESS DATA MANAGEMENT

RELATED APPLICATIONS

This application claims priority from commonly assigned Provisional Application SN 60/928,179, filed May 8, 2007 and is also a continuation-in-part of Utility application Ser. No. 12/150,806, filed May 1, 2008.

BACKGROUND OF THE INVENTION

Over the last several decades, biotechnology has become increasingly fundamental to our society and now has a major impact on the production of food, medicine, fuel, and materials. This importance and influence on our day to day lives has lead to a desire to better monitor and control the processes used to implement this technology. In part due to these reasons, and to end a stagnant period in the technological advancement of drug development, the US FDA has created the PAT (Process Analytical Technology) initiative (http://www.fda.gov/cder/OPS/PAT.htm). This initiative encourages not only large pharmaceutical manufacturers but also smaller modern biotech companies to bring new technological advances into mainstream use to help modernize and optimize biotech manufacturing. Much of the impetus for the PAT initiative is to bring about advances in monitoring and control so that drug manufacturing is safer, more repeatable, more transparent, and less expensive and thereby protect the public. For example, in the "Process Control Tools" section of the PAT guidance document, it states that:

"Strategies should accommodate the attributes of the input materials, the ability and reliability of the process analyzers to measure critical analytes, and the achievement of process endpoints to ensure consistent quality of the output materials and final product." Design optimization of drug formulation and manufacturing and processes within the PAT framework can include the following steps:

Identify and measure critical material and bio-process attributes relating to product quality Development of a process measurement system that allows real-time or near real-time (e.g. on-line or at-line) monitoring of critical bio-process/product attributes Design process controls that enable adjustment to ensure that critical process parameters are controlled Develop mathematical relationships between product quality attributes and measurements of critical material and process attributes Much of this can be summarized to mean that by using advanced monitoring of materials used and process variables (e.g.: pH, dissolved oxygen, dissolved $CO_2$, glucose, glutamine, lactate, ammonia) mathematical models of a bioprocess can be created. Through the use of these models, the process yield can be predicted and thereby lead to optimized growth runs even if every process parameter is not fully understood. Once monitoring systems are in-place and models created, advanced control systems can be used to implement the optimization procedures.

In the future, for a typical microbial or cell growth run to conform to the PAT initiative as outlined above, it is likely that all the raw materials and also the data used in the growth process will need be recorded and tracked. For instance, the growth media manufacturer's formulation specifics, lot data and manufacture date will need to be logged so that issues like contamination, expiration, or other factors affecting quality or performance can be tracked. The same will be true for the actual cell line used, the pH buffer employed, the glucose feed, the sensor manufacturing data, and other inputs. As the trend towards disposable bioreactors, disposable sensors, and other disposable materials mature and become a major part of the manufacturing chain these items will need to be tracked as well.

BRIEF DESCRIPTION OF THE DRAWINGS

FIG. 1(a) prior art use flow, versus FIG. 1(b) use flow in accordance with the present invention. It should be noted that although the present system will be referred to as a "data management" system, its applicability encompasses process and process component monitoring (tracking and/or calibration) and also control of a bioprocess.

FIG. 5(a) prior art data flow, versus FIG. 5(b) data flow in accordance with the present invention.

DESCRIPTION OF THE INVENTION

Figure 1A:
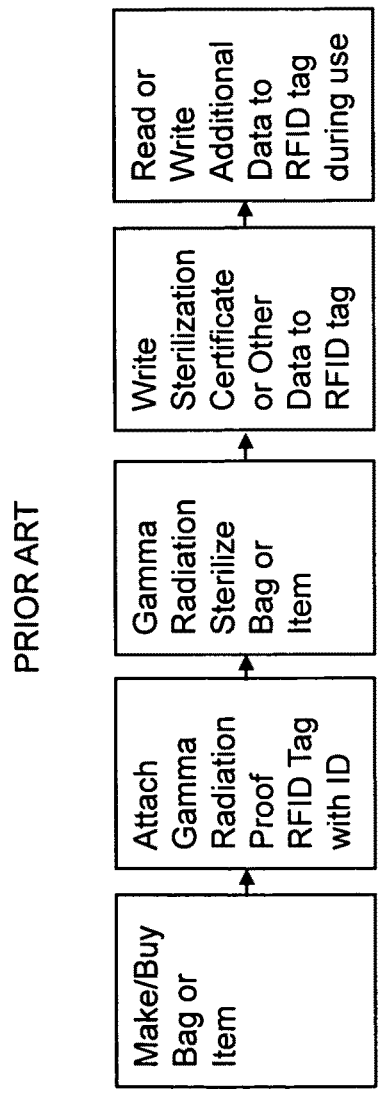
FIGS. 1a and 1b are flow charts showing a two different process flows for using a radio frequency identification (RFID) tag as a tracking system for single-use bioprocess components.

Our invention specifically addresses the need for automated data acquisition by a control system in bio-process manufacturing. For the tracking of any element (e.g., sensor, other component or bio-process ingredient) used in a bio-process, and in order to adhere to the concepts put forth in the PAT initiative, the bioprocess data management (control) system will need to record information that contains, but is not limited to:

1. Calibration and/or performance data
2. Serial and lot numbers
3. Material certifications
4. Aging information This information can be automatically loaded into a control system or a transmitter that interfaces with the element to be interrogated using a variety of means as discussed in detail below. A transmitter here connotes a device that: i) connects to a probe or non-volatile memory device and supplies it with power, ii) can access the probe or read stored information, and iii) has a human/machine interface (HMI) so that the data can be displayed and understood. After the data is retrieved, it can be utilized by the control system or by the transmitter to optimize the bio-process performance or the data can be displayed and/or logged as part of the data management system. For example, a sensor such as a dissolved oxygen or pH sensor can have its calibration data automatically retrieved in this way. The optimal control algorithm, including growth and feeding strategy, can be automatically implemented if the cell line and growth medium are known, provided only that this information is preprogrammed into the control system. Additionally, any regulatory agency information required can be recorded with the growth run data, provided the material certifications and lot numbers containing this information are automatically read into the system from the non-volatile memory device or other information storage device.

The information required to describe, control, and/or automate a modern biotech process will vary in both scope and quantity. Depending on the volume and sophistication of the data, it can be recorded and read back using a variety of methods. These methods include:
1. RFID chip
2. Nonvolatile memory/EEPROM
3. Internet download
4. Other means to semi-automatically read labels or tags such as holographic stored data markers or fluorescent nano-tags.

The data itself can be embedded in a label, tag, non-volatile memory (e.g.: FRAM), or RFID or surface acoustic wave (SAW) chip.

The prior art (e.g., US2005/0205658 or US2007/0200703), primarily describes a data tracking system, wherein a serial number is encoded in a RFID tag that is attached to equipment or components being monitored. The RFID tag is used to retrieve product information such as the lot number, date of manufacture, materials certificate numbers, and expiration date, from a database on a PC over an internet link. The RFID tag can also have read-write capability, so that the tracking system can capture data relating to the exposure of the equipment or component to processes or environments that can damage it, such as sterilization by autoclaving or chemical cleaning. The RFID tag is resistant to these cleaning processes and can be re-read many times during the course of the use of the component or equipment. The overall purpose of the prior art system is to track the aging of the equipment or component, so that its failure date can be predicted for scheduled maintenance, and it can automatically be re-ordered and restocked. The prior art describes collecting data from many samples into a database, in order to estimate the useful life and time to replacement for the component or equipment.

Figure 1B:
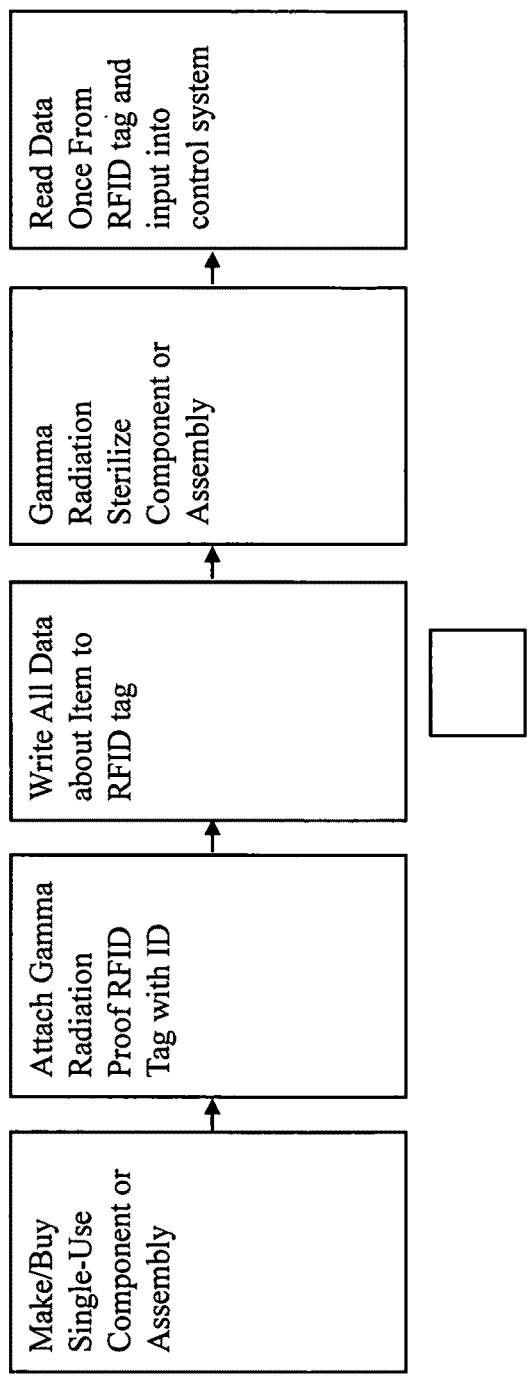

The prior art pertaining to RFID tags used on single-use bio-process equipment or components (e.g., US2008/0024310A1) that are sterilized by gamma irradiation, specifically states that the product tracking information such as serial and lot numbers should be stored on the gamma radiation resistant portion of the tag, but also that additional information, such as the radiation dose, is entered on the tag post irradiation. FIG. 1(a) illustrates the process flow for the RFID tags described in US2008/0024310A1. Therefore, the use case of the tag in the above-indicated Published Patent Application requires that at least a portion of the RFID tag memory must be gamma radiation resistant, a requirement that is satisfied by the FRAM technology utilized by companies such as Fujitsu and others. In contrast, the present invention describes labels, including but not limited to RFID tags, where the entirety of the information pertaining to the component is entered prior to the final sterilization step, rather than as a sequence during the manufacturing or assembly process for the component (e.g., filling a bag with media, or inserting a sensor into a bioreactor liner bag). The process flow for the present invention is shown in FIG. 1(b).

Unlike the present invention, the prior art does not describe or suggest a label or tag that carries process-specific or sensor calibration data, and also is usable to control a bio-process and/or measure parameters of the bioprocess in real-time. The prior art also assumes that the data is both written to and entered from an external database rather than a transmitter and/or controller directly associated with both the bio-process and the component being used. Finally, the prior art assumes that the RFID tag is writeable (can be written to) and that the user will input more than one process event on the tag. In the present invention, the label (tag) is exclusively associated with a single-use component, and is therefore read only once, at the start of the bio-process, because it is discarded after the bio-process is complete. Other prior art pertaining to water quality monitoring tools (e.g., U.S. Pat. No. 7,007,541) is primarily aimed at re-usable sensors whose calibration constants change with aging or interchangeable sensors where the re-usable sensor heads are each unique enough that their parameters need to be accounted for systematically.

Figure 2:
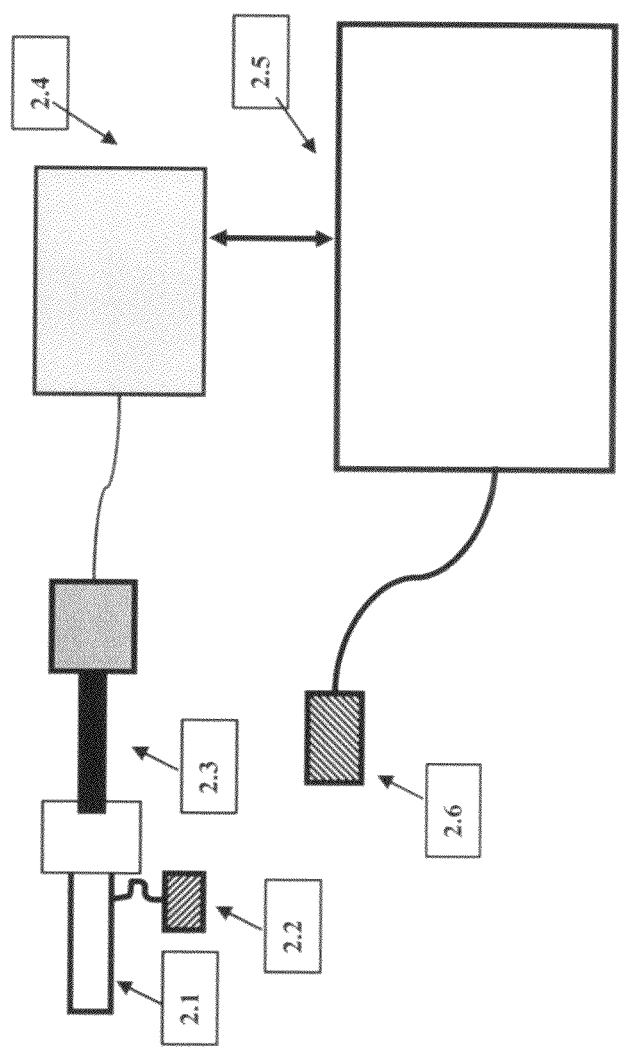
FIG. 2 is a schematic showing an example of a single-use bioreactor tracking system in accordance with the present invention.

When using a semi-automatically-readable (take to reader) label (tag) such as a set of magnetic stripes (or equivalent marking system) or a memory device based on SAW (surface acoustic wave) chips, the reading of the data will advantageously be semi-automated. In the present context semi-automated means that the user will not need to manually enter the data describing the component, and will only need to bring a reader into sufficiently close proximity and with a specific orientation in order to accomplish the data transfer to the reader. An example in accordance with the present invention is shown in FIG. 2. In FIG. 2, 2.1 is a disposable element on which an encoded label 2.2 resides, 2.3 is a re-useable element, and 2.4 is the transmitter to which 2.3 is connected, 2.5 is an automation system that consists of both control software and hardware. A label reader 2.6 is shown connected to the automation system. Since the system is in communication with the transmitter 2.4, the label 2.2 information can be used by the transmitter. The disposable element 2.1 can, for example, be a disposable sensor, a disposable (single use) bioreactor vessel, a container of a particular microbe or cells from a cell bank, growth medium, pH buffer, or any other input or process variable used in a growth run or similar biotechnology process.

Another level of automation is the use of a non-volatile memory storage component such as FRAM (ferro-electric based random access memory chip) or an EEPROM (Electrically Erasable Programmable Read-Only Memory) chip (equivalent functionality to a label) to store data and provide an interlock for the system. A system using non-volatile memory chips such as a FRAM or an EEPROM can be employed for any component that is plugged into (i.e., is physically connected to) the system. For instance, if using a disposable bioreactor vessel and/or a set of disposable sensors, the disposable elements can be plugged into the data management (control) system of the present invention. For example, if the bioreactor under study is a disposable bioreactor or bioreactor using disposable elements, the recorded information regarding the date of manufacture, the materials used and their certifications, (e.g.: growth media, sensor calibration data etc.) can all be automatically loaded into the control system memory from the nonvolatile memory after it is plugged into the system. A FRAM based nonvolatile memory is inexpensive and therefore can be readily disposed of with the disposable component after a single use.

Figure 3:
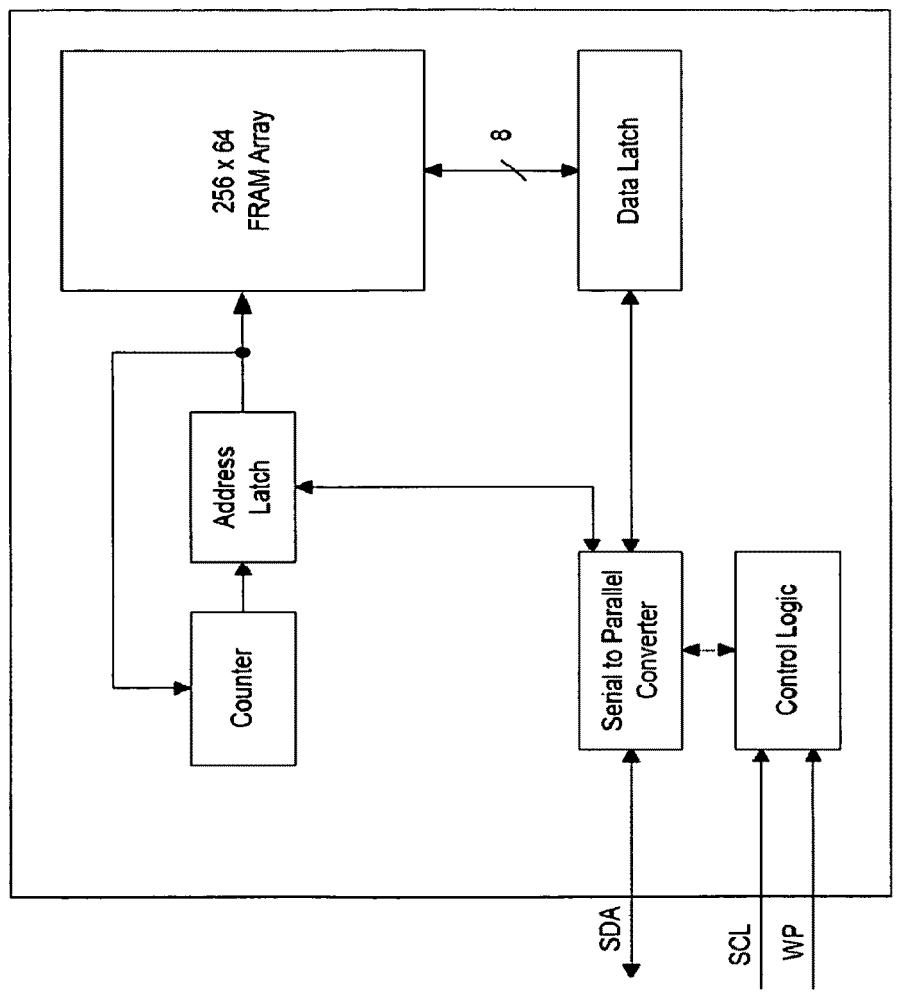
FIG. 3 shows the block diagram of a typical gamma radiation resistant ferro-electric random access memory (FRAM) nonvolatile memory chip

The gamma radiation resistant, nonvolatile memory allows for the transfer of calibration or other information from the factory to the apparatus without concern for the possibility of operator error. This is a significant advance over the current state of the art which calls for an operator to enter this type of information via a keypad or by scrolling through alpha numeric characters one at a time. Any particular (or all) information can be encrypted in order to verify its authenticity and to protect it from alteration or tampering. This also allows the manufacturer to provide a unique identification code for each device/component for traceability purposes. This unique identification code thus allows the data management (control) system to control the number of times, duration, or conditions under which the component is used, and can therefore be used to prevent reuse, misuse and fraud. Such misuse can, for example, include trying to use pre-sterilized disposables more than once. FIG. 3 shows a block diagram of a FRAM-based, non-volatile memory chip. EEPROM's can also be obtained that are gamma radiation resistant, but to date these devices are more expensive and therefore somewhat less appealing in certain cases.

Figure 4:
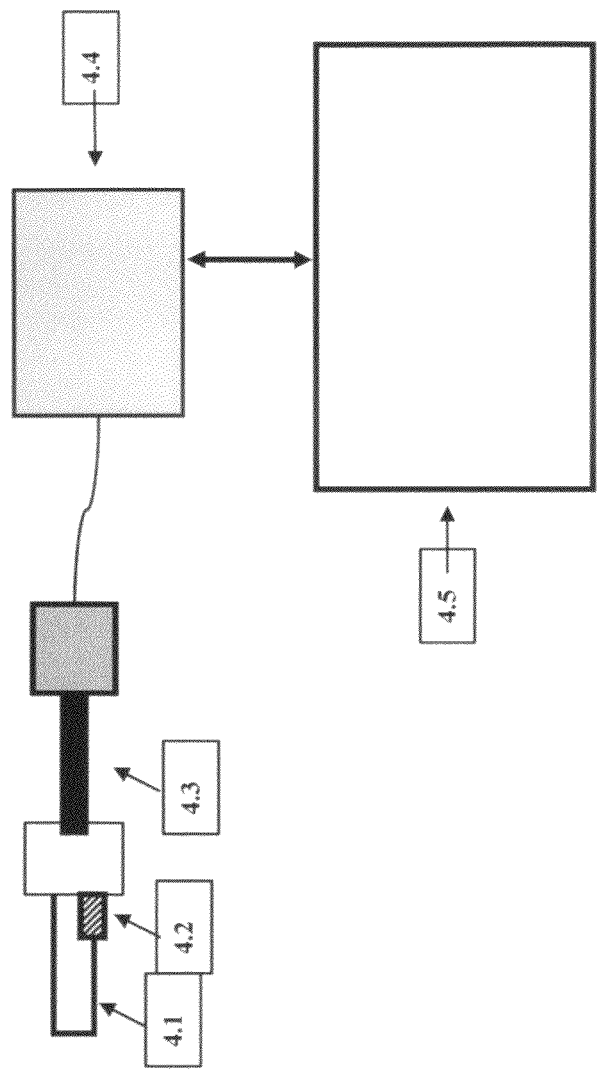
FIG. 4 is a schematic showing portions of a data management system in accordance with the present invention which can suitably utilize a FRAM chip.

FIG. 4 depicts a typical application using a control system in accordance with the present invention. In FIG. 4, 4.1 is the disposable element, 4.2 is the FRAM or equivalent non-volatile storage element, 4.3 is a re-usable element or reader into which 4.1 is connected, 4.4 is a transmitter which can optionally interact with either the re-usable element 4.3 or with the FRAM. When the disposable element 4.1 is connected to the reusable element 4.3, the data in the FRAM is read and processed as discussed above. The automation system, 4.5, is connected to the transmitter, and can act as the master controller or the repository for data read into the transmitter. Element 4.1 can be a disposable sensor, a disposable element for a bioreactor such as a valve or bag or a similar single-use item. As many of the disposable or single-use components in a bioprocess are relatively small, the size of the FRAM can be important. Many non-volatile memory storage components (chips) are physically large in order to help enhance their gamma radiation resistance which can pose a problem for locating the memory device on the disposable component. In general, chips that are similar in shape to a standard SOIC (small outline integrated circuit) package or a flat-pack with leads coming from all 4 sides of the chip will advantageously be utilized. The optimal chip will therefore preferably have a surface area no larger than about 1 cm$^2$ and be no thicker than about 1 mm and most preferably be approximately 6 mm×6 mm and 0.5 mm thick.

A similar result can be accomplished through the use of an RFID-based tagging system. Similar to the nonvolatile memory and the label systems described above, this embodiment of the present invention enables one to perform the following functions:

1. Transfer data and information from the manufacturer's calibration database or data storage to the control system without operator error.

2. Eliminate time consuming manual data entry via a keypad or by sequentially scrolling through alpha numeric characters one at a time.

3. Encrypt data and information to guarantee its authenticity.

4. Transfer information without out any physical contact or particular orientation of the RFID tag.

5. Provide a log of each unique identification tag for traceability, as well as to minimize possibility of misuse or fraud.

Figure 5A:
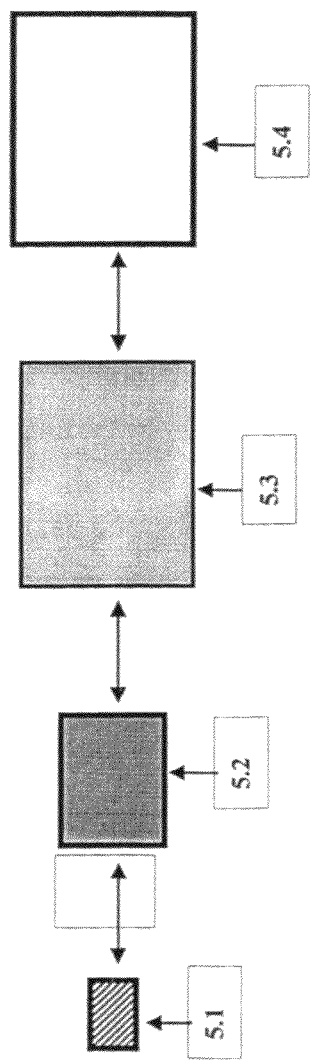
FIGS. 5(a) and 5(b) show two examples of single-use bioreactor tracking systems and their integration into the overall data management and control system.

A benefit resulting from using an RFID tag system is that the identification system does not need to be physically attached to the disposable element. This method enables one to tag the disposable element or disposable sensor instrument (or the package that contains it), such that it can be tracked from manufacturing to final use. The RFID tag preferably includes a unique identification number. The tag also carries the aforementioned information in its nonvolatile memory. The information is advantageously encrypted and checksummed in order to prevent tampering and/or invalid calibration. In one example (FIG. 1(b), the RFID tag is attached to the disposable element and product specific information is entered on the tag prior to sterilization. The RFID tag is then sterilized together with the disposable element (component). For example, if this is a sensor, it will be the calibration data and other applicable manufacturing information; for a disposable bioreactor, it can be the films used; for growth medium, it can be the lot and serial number for process tracking. This RFID tag system can be used with any disposable bio-process components that will benefit from having information managed. The size of the RFID tag can be important as the efficacy is related to the size. The larger the RFID tag's area, typically the larger the antenna of the tag and hence the greater distance it can be from a reader and still be read. However, smaller tags with the antenna constructed of multiple loops are also effective and are therefore preferred. In general, the tag needs to be large enough to satisfy the distance requirements for its use, yet small enough that it can still be packaged with the single-use component which needs to be tracked, calibrated, or otherwise have its data managed. The RFID tag will therefore preferably have a substantially planar configuration and a surface area no greater than about 150 cm$^2$ In the prior art techniques, the data flow to and from the label on the disposable element bypasses the automation system associated with the bioprocess in which the disposable element is used. FIG. 5a illustrates the data flow as described in published applications US2005/0205658, US2007/0200703, and US2008/0024310A1. In these cases data from RFID tag 5.1 is read or written by reader 5.2 to computer 5.3 that links into an external database 5.4. Database 5.4 is either stored on computer 5.3 or is external, with Ethernet access from computer 5.3. Such data flow is appropriate for a system that is associated with manufacturing quality, materials requirements planning, or enterprise resource planning systems. Such a prior art system can generate a database that provides information to estimate useful service life and time to failure for components, as well as an ability to re-order inventory. However, such a database is only useful for the control of a bio-process system in the event of a process failure, when materials certificates and serial numbers must be accessed for a root cause analysis of the failure.

Figure 5B:
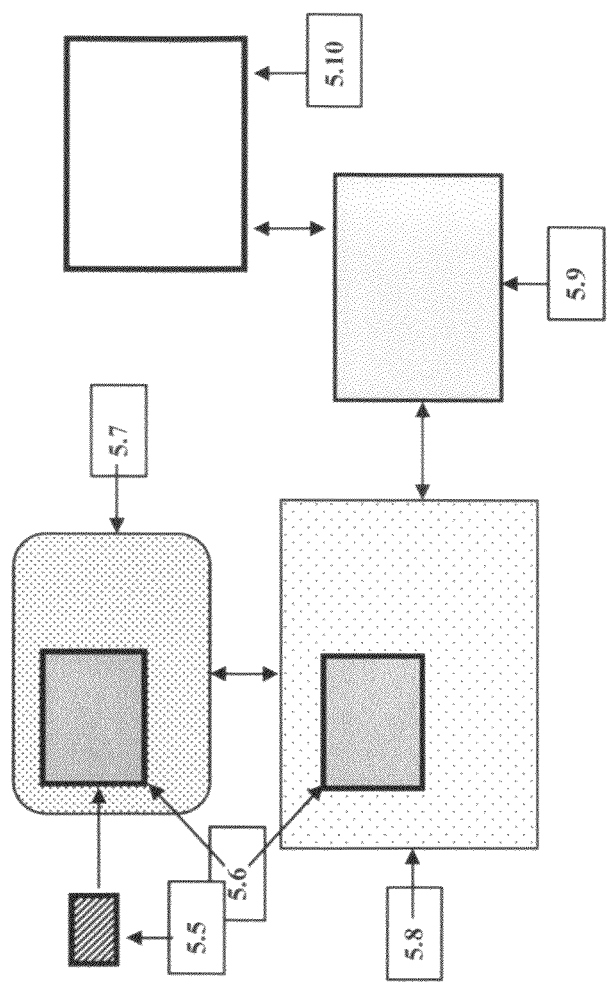

In the present invention, as in the embodiment shown in FIG. 5b, the data flow from the disposable element label 5.5 occurs through reader 5.6 into either transmitter 5.7, whose output is connected to controller 5.8, or directly into controller 5.8. The process data containing the label information is then saved in 5.9 (the system historian or historical database) as part of the batch record, or as a process parameter. The data from label 5.5 is used either by transmitter 5.7 or controller 5.8 during the bio-process, in order to effect control of the bio-process. For example, calibration constants can be used by the transmitter to calculate sensor output values that are sent to the bio-process automation system, which then actuates pumps or mass flow control valves; or the amino acid concentration in the media of a pre-filled bioreactor bag is used by the control system to predict feeding and cell growth rates after inoculation. In both of these examples, the data from the label/non-volatile memory is actively used to control the bio-process, and generates additional, associated process data that can be used to characterize the effectiveness of the disposable element in the process for future runs. This use of disposable labels is equally applicable to upstream (cell culture/fermentation), downstream (purification), or fill-finish bio-processes.

Furthermore, the control system 5.8 can be linked to a materials requirements planning system within the fabrication facility 5.10, such as SAP or Oracle, update the inventory levels automatically after the completion of the process using the disposable element, and input process feedback into the plant management system. Unlike the prior art, which requires human intervention to an external database, this inventory management can be performed completely automatically using the data management system of the present invention.

In the present invention, the ID number that is stored on the label or other non-volatile memory may correspond to product specification information for the component, such as materials certifications, lot numbers, manufacturing date, and/or sterilization records. This information can be stored in a remote database, for example, a section of the supplier's database that is only accessible by the end user or OEM customer. In contrast to the prior art, where the informational database must be accessed manually by the user, in the present invention, the database URL address and an optional encrypted key-code for remote database access are also stored on the label or tag and are read out by the transmitter or automation system. If either transmitter or automation system is connected to the internet via the Ethernet, it can automatically access the URL, enter the optional key-code, and automatically gain access to the database information, in order to download it and store it in the process batch record. Alternatively, if the bio-process automation system and/or transmitter are programmed to have their own user ID and password to the database and the URL has been already entered into their memory, only the component's ID number required from each label or tag, and database access remains automatic.

Most systems in accordance with the present invention will utilize a disposable element such as a sensor element or a disposable element that comprises a sensor element, a reusable component that holds the electronics measuring the sensor response and which interfaces to the transmitter, and also an RFID tag having both a unique identifier and a nonvolatile memory element. A process for utilizing the system of the present invention would proceed according to the following steps:
1. The disposable (e.g.: sensor) element is first calibrated using a known method.
2. After the calibration and performance data for the disposable element is generated, it needs to be associated with the single use component for which the data was generated in the bio-process.
3. The disposable element is sealed in a bag with a visible identifying number or tag, such as a paper label.
4. The bag containing the disposable element is gamma irradiated and a RFID tag is applied to the outside of the bag.
5. A computer program encodes the calibration information on the RFID tag, along with any additional information pertaining to the disposable element, such as material certificate numbers, batch numbers, etc.
6. This information is stored in the RFID tag's nonvolatile memory elements.
7. The RFID tag's unique identifier is recorded visibly on its exterior for ease of identification.

Once the disposable element is ready to be used, it is taken to the reusable element where a scanner (reader) reads the data from RFID tag, both the unique identifier and also the nonvolatile memory elements. The reusable element will have an associated transmitter or processor that decodes and applies the information it has read from the RFID tag. The disposable element can now be used with minimal intervention by the end user. If this is a sensor, it is now ready to take measurements; if it is disposable bioreactor system then all of the relevant data on the bag, the growth media, configuration, batch ID, etc., is now entered into the control system.

Figure 6:
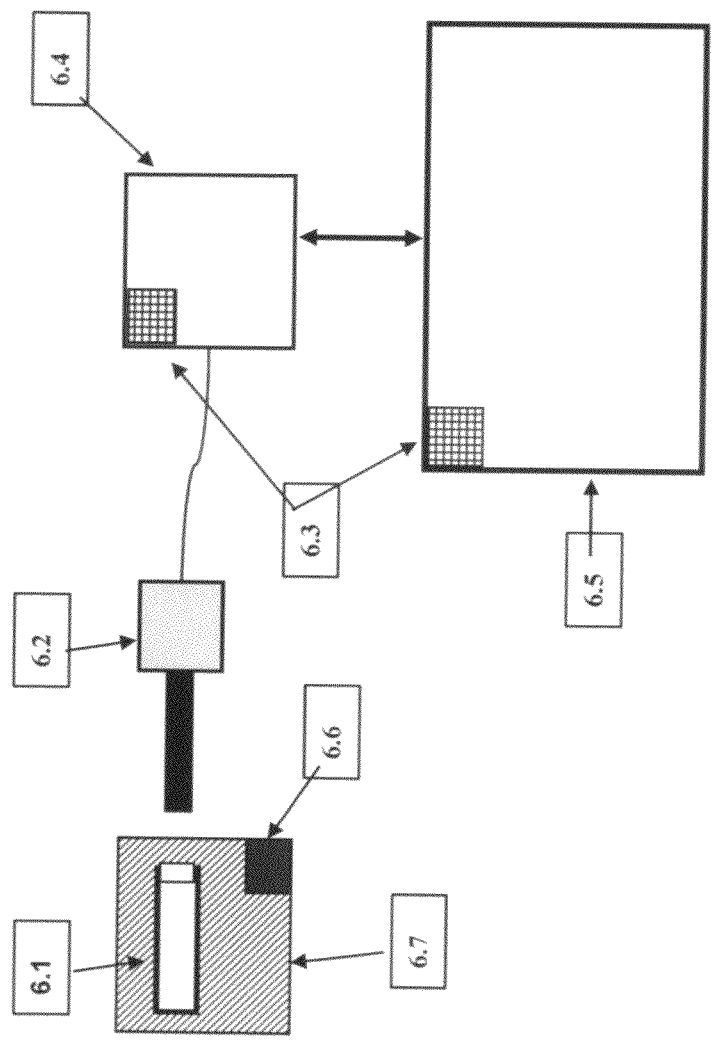
FIG. 6 shows a part of a bio-process control system in accordance with an alternative embodiment of the present invention where the RFID is directly attached to the disposable element (e.g., a dissolved oxygen probe) prior to packaging or sterilization, and the tagged disposable element is incorporated within a disposable assembly.

Note that in the embodiment illustrated in FIG. 6, 6.1 is the disposable element, 6.2 is the reusable element, and 6.3 are the RFID readers which can be located either in the transmitter 6.4 or the automation system 6.5. The RFID tag 6.6 is directly attached to the disposable element 6.1, and the calibration or other data is written onto the non-volatile memory of the RFID tag using a computer. The disposable element may then either be integrated into a larger assembly 6.7, such as a bioreactor bag for a disposable sensor or component and packaged in a bag 6.8, or be separately and directly packaged in a bag 6.8. The assembly 6.7, including any attached RFID tags, is then sterilized, either individually, or as a group on a pallet. When the assembly 6.7 is used in a bio-process, used each tag is removed from its associated component and scanned into the system.

Figure 7:
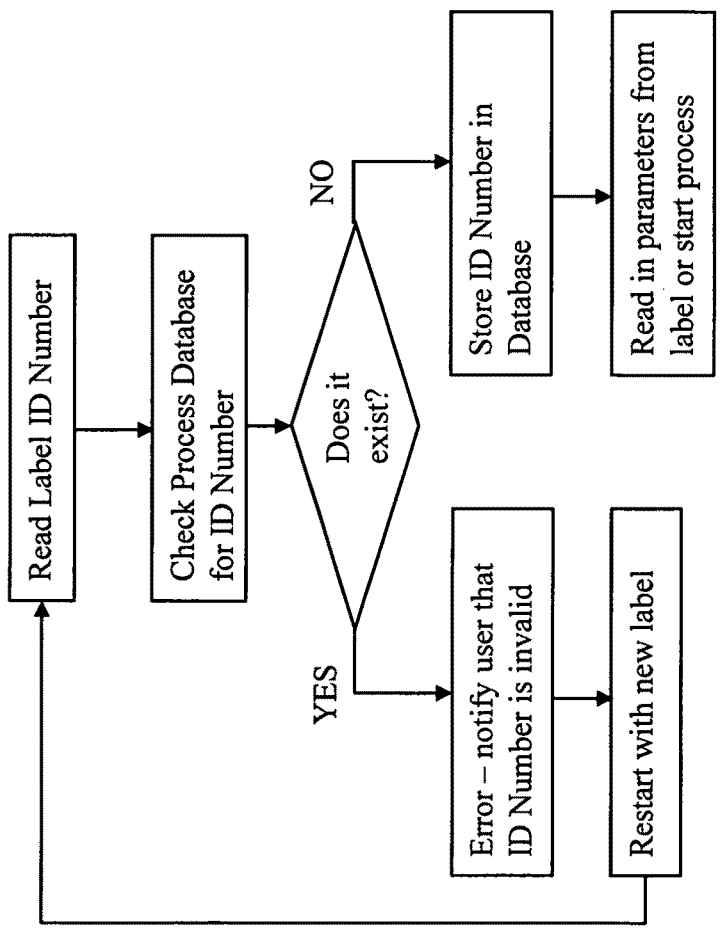
FIG. 7 shows a flow diagram accordance with the present invention showing how to implement label security, to ensure that a single-use component is used only once.

The re-usable element, or the system to which the re-usable element is connected, will also preferably have its own non-volatile storage. This memory can be used to log the usage of the disposable elements. For example, this usage log can be utilized to verify that the disposable element has never been used before. If the unique identification number has been used before or does not conform to a validation algorithm, the identification is invalidated and a warning to this effect is given through the interfaces. The architects of the system can decide how much or how little to minimize the user's activity. FIG. 7 shows an example of a flow diagram associated with RFID security, so that a single-use component cannot be re-used, and thereby not cross-contaminate a subsequent process.

Figure 8:
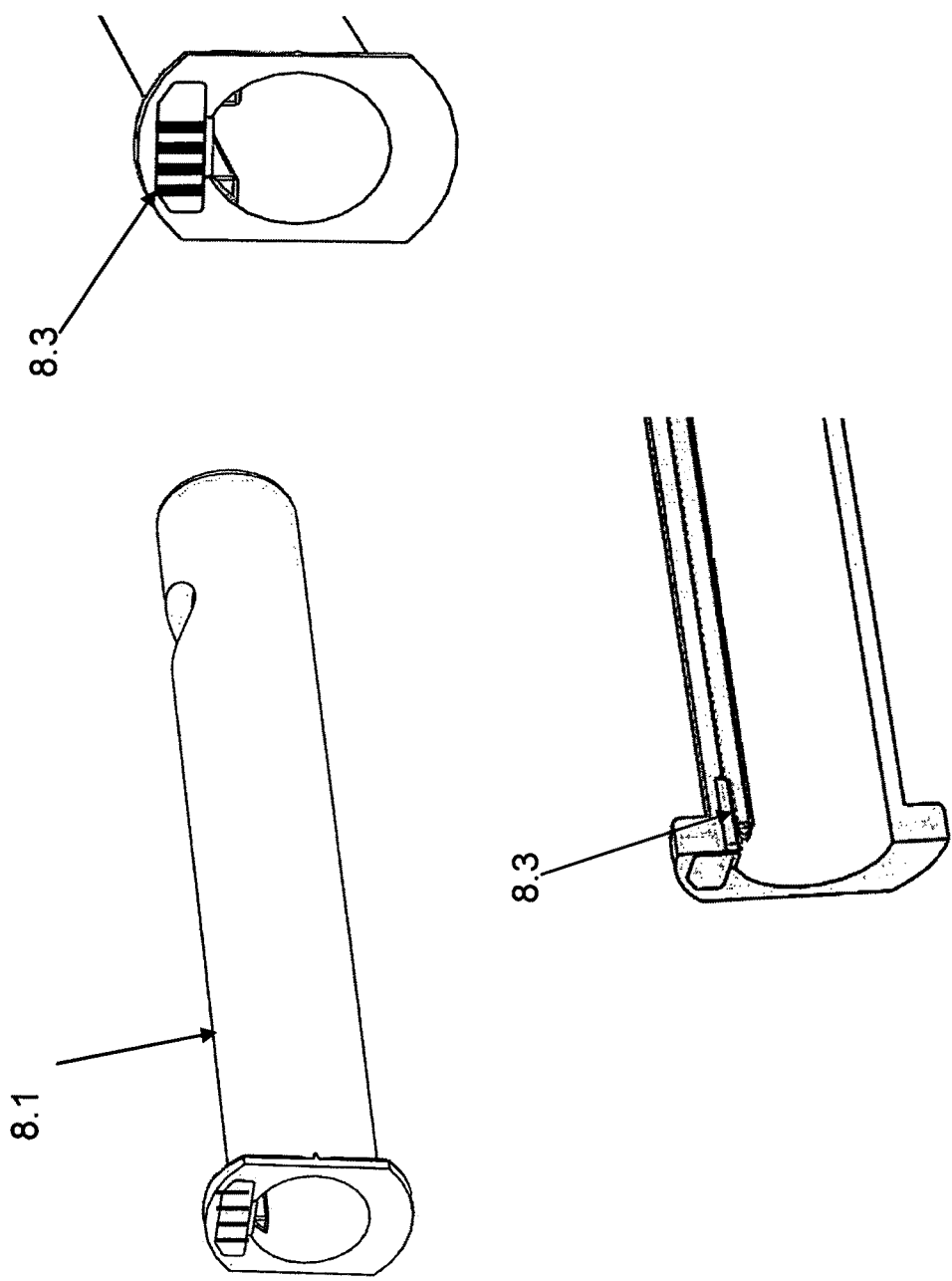
FIG. 8 shows overall and also end and partial cut away side views of a disposable sensor assembly suitable for the practice of the present invention.

Referring now to FIG. 8, there is illustrated overall (8.1) and also end and partial cut away side views of a disposable sensor assembly suitable for the practice of the present invention. 8.2 denotes electrodes which enable the non-volatile memory (such as a FRAM) 8.3 to interface with the transmitter such as that designated as 5.7 in FIG. 5.

The invention claimed is:
1. A data management and calibration system for use with sensors and control systems for a biological process, the data management and calibration system comprising:
   i. a disposable single-use component comprising electrodes and a sensor, the disposable single-use component being configured to measure a process control parameter directly applicable to the biological process,
   ii. a non-volatile memory storage component which is permanently affixed to the single use component and which is programmed prior to gamma irradiation of the memory storage component and the single use component to which it is affixed, both the single use component and the memory storage component not being adversely affected by gamma radiation, the memory storage component including a unique identification code, a memory, and at least one already entered, prior to gamma irradiation, data element that provides a calibration parameter for calculating sensor output values from the single use component to thereby enable the single use component to measure the process control parameter in real time, wherein the non-volatile memory storage component is configured to be non-writable by a user after gamma irradiation, and iii. a memory reading system comprising at least a reader in physical contact with the memory storage component and which supplies the memory storage component with power and which also functions to: a) obtain the unique identification code and the calibration parameter from the memory storage component, b) utilize the calibration parameter to enable the single-use component to measure the process control parameter, and c) transmit a measured process control parameter to a biological process control system, wherein the electrodes enable the non-volatile memory storage component to interface with the memory reading system.

2. The data management and calibration system of claim 1 wherein the process control parameter is pH, dissolved oxygen, dissolved $CO_2$, temperature, pressure, level, foam, cell density, cell viability, an anti-foam additive, an amino acid, a bio-process end product comprising a protein, antibody or plasmid, or a metabolite selected from the group consisting of glucose, lactate, glutamine, glutamate and ammonia.

3. The data management and calibration system of claim 1 wherein the memory reading system is a component of the biological process control system.

4. The data management and calibration system of claim 3 wherein the biological process control system is utilized in conjunction with a disposable bioreactor.

5. The data management and calibration system of claim 1, wherein the data element comprises at least one calibration constant for the sensor.

6. The data management and calibration system of claim 1, wherein the data element describes at least one critical additive present in a biological process media.

7. The data management and calibration system of claim 1, wherein additional information is stored in the memory storage component, and the additional information includes information selected from the group consisting of a manufacturing date, a batch number, a lot number, a material specification, a material lot number, a certification for sterility, a certificate of compliance, a size specification, a functional specification, a description of the single use component, an expiration date, process data, calibration data, lifetime data, composition data, and customer application data associated with the unique identification code.

8. The data management and calibration system of claim 7 wherein the additional information is used by the biological process control system to ensure that the disposable single use component is used only once.

9. The data management and calibration system of claim 1 wherein the non-volatile memory storage component has a surface area no larger than 1 $cm^2$ and is no thicker than 1 mm.

10. The data management and calibration system of claim 1 wherein the single use component and the affixed non-volatile memory storage component are integrated into a disposable single-use bioreactor assembly prior to gamma irradiation sterilization of the disposable single-use bioreactor assembly.

11. The data management and calibration system of claim 10 wherein the disposable single-use bioreactor assembly comprises a bioreactor bag.

12. The data management and calibration system of claim 1, wherein the disposable single-use component and the non-volatile memory storage component are configured to be physically connected to the memory reading system when utilizing the calibration parameter.

13. The data management and calibration system of claim 12, wherein the disposable single-use component comprises four electrodes.

14. The data management and calibration system of claim 1, wherein the non-volatile memory storage component is a ferro-electric RAM.

15. A method of data management and calibration for controlling a biological process, comprising in sequence the steps of:
   i) permanently affixing a non-volatile memory storage component to a single use component configured to measure a process control parameter for the biological process, the non-volatile memory storage component having a unique identification code and both the non-volatile memory storage component and the single use component being gamma radiation resistant,
   ii) entering calibration data for calculating sensor output values from single use component to thereby enable the single use component to measure the process control parameter from the single use component on the non-volatile memory storage component,
   iii) after ii), gamma radiation sterilizing the single use component and the affixed non-volatile memory storage component, wherein the non-volatile memory storage component is configured to be non-writable by a user after gamma irradiation,
   iv) after iii) reading and validating the unique identification code present on the non-volatile memory storage component, and reading and using the calibration data entered on the non-volatile memory storage component to measure the process control parameter, wherein the unique identification code and the calibration data are transmitted from the non-volatile memory storage component through electrodes that interface with a memory reading system,
   v) transmitting a measured process control parameter to a control system for controlling the biological process, and
   vi) discarding the non-volatile memory storage component and the affixed disposable single use component after completion of the biological process.

16. A method in accordance with claim 15 further comprising entering an encrypted URL on the non-volatile memory storage component prior to iii).

17. A method in accordance with claim 15 wherein the single use component and the affixed non-volatile memory storage component are integrated into a single-use bioreactor assembly prior to gamma radiation sterilization of the single-use bioreactor assembly.

18. A method in accordance with claim 15 wherein entry of all desired performance, control and/or calibration data applicable to the single use component on the non-volatile memory storage component is effected when the non-volatile memory storage component is fabricated.

\* \* \* \* \*